United States Patent [19]

Huenig et al.

[11] Patent Number: 4,578,220
[45] Date of Patent: Mar. 25, 1986

[54] CHARGE TRANSFER COMPLEXES OF TETRATHIO/SELENO-FULVALENE DERIVATIVES AND BISCYANIMINE DERIVATIVES; BISCYANIMINE DERIVATIVES AND METHOD FOR PRODUCING SAME

[75] Inventors: Siegfried Huenig, Wuerzburg; Alexander Aumueller, Lichtenfels, both of Fed. Rep. of Germany

[73] Assignee: BASF Aktiengesellschaft, Ludwigshafen, Fed. Rep. of Germany

[21] Appl. No.: 662,049

[22] Filed: Oct. 18, 1984

[30] Foreign Application Priority Data

Oct. 19, 1983 [DE] Fed. Rep. of Germany ....... 3337887

[51] Int. Cl.[4] .................. C07C 121/54; C07D 409/04; C07D 421/04; C09K 15/58
[52] U.S. Cl. ........................... 260/239 R; 260/396 N; 564/103; 252/299.3; 502/158; 502/168; 502/175; 549/30; 549/32; 549/33; 549/35; 549/36; 549/37
[58] Field of Search ........... 260/465 E, 465 R, 239 R, 260/396 N; 252/299.3; 502/158, 168, 175; 549/30, 32, 33, 35, 36, 37

[56] References Cited

PUBLICATIONS

Narita et al., Synthesis, 1976, pp. 489–514.
Aumueller et al., CA, vol. 101, 1984, 101:38192f, p. 484.

Primary Examiner—Henry R. Jiles
Assistant Examiner—J. G. Mullins
Attorney, Agent, or Firm—Oblon, Fisher, Spivak, McClelland & Maier

[57] ABSTRACT

A novel charge transfer complex of an N,N'-biscyanoquinone bisimine of the formula

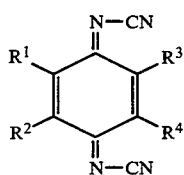

and a fulvalene derivative of the formula

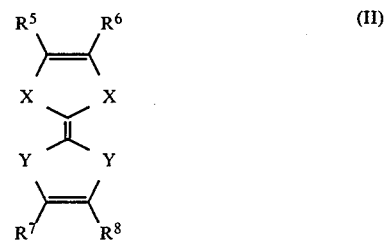

where, in formula I, $R^1$, $R^2$, $R^3$ and $R^4$ independently of one another are —H, —$CH_3$, —$C_2H_5$, —$OCH_3$, —$OC_2H_5$, —Cl and/or —Br, and one of the radicals $R^1$ and $R^2$ and/or one of the radicals $R^3$ and $R^4$ may furthermore be phenyl or tert.-butyl, or $R^1$ and $R^2$ and/or $R^3$ and $R^4$ together form

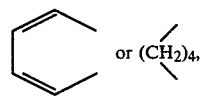

and the fused-on aromatic ring is unsubstituted or substituted, and, in formula (II), $R^5$, $R^6$, $R^7$ and $R^8$ independently of one another are each —H, —$CH_3$, —$C_2H_5$, phenyl, methylphenyl or methoxyphenyl, or $R^5$ and $R^6$ and/or $R^7$ and $R^8$ together form

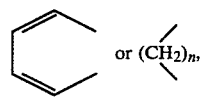

where n=3, 4 or 5,

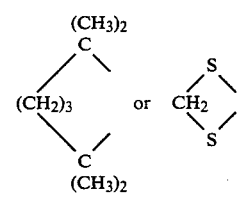

and X and Y indendently of one another are each S or Se.

In the crystalline state, the charge transfer complex possesses electrical conductivity and accordingly can be used as an electrical semiconductor or photoconductor.

Novel biscyanoquinone imines of the formula (I), where $R^1$, $R^2$, $R^3$ and $R^4$ have the stated meanings, and a novel process for the preparation of the compounds (I).

13 Claims, No Drawings

CHARGE TRANSFER COMPLEXES OF TETRATHIO/SELENO-FULVALENE DERIVATIVES AND BISCYANIMINE DERIVATIVES; BISCYANIMINE DERIVATIVES AND METHOD FOR PRODUCING SAME

The present invention relates to novel charge transfer complexes based on biscyanimines.

Charge transfer complexes of tetrathio/selenofulvalenes and tetracyanoquinodimethanes have been disclosed (Synthesis 1976, pages 489/514, and J. Chim. Phys. 79 (1982), 299 et seq.).

The present invention relates to novel charge transfer complexes of a biscyanimine of the formula

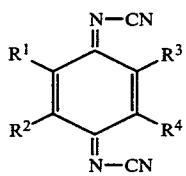
(I)

and a compound of the formula

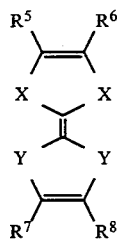
(II)

where $R^1$, $R^2$, $R^3$ and $R^4$ independently of one another are each hydrogen, methyl, ethyl, methoxy, ethoxy, chlorine or bromine, or one of the radicals $R^1$ and $R^2$ and/or one of the radicals $R^3$ and $R^4$ is phenyl or tert.-butyl, or $R^1$ and $R^2$ and/or $R^3$ and $R^4$ together are each a

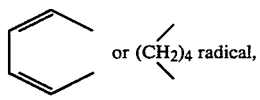 or $(CH_2)_4$ radical, in which the fused-on aromatic rings are unsubstituted or monosubstituted or disubstituted by chlorine, bromine and/or methyl, $R^5$, $R^6$, $R^7$ and $R^8$ independently of one another are each hydrogen, methyl, ethyl, phenyl, methylphenyl or methoxyphenyl, or $R^5$ and $R^6$ and/or $R^7$ and $R^8$ together form a

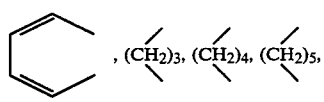, $(CH_2)_3$, $(CH_2)_4$, $(CH_2)_5$,

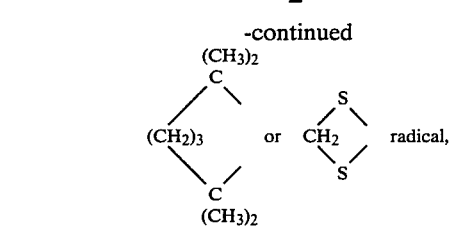 radical, and X and Y independently of one another are each S or Se.

In the charge transfer complexes, the molar ratio of acceptor to donor is, as a rule, 1:1. However, in the case of charge transfer complexes which contain dibenzotetrathiafulvene ((II) where $R^5/R^6$ and $R^7/R^8$ are each

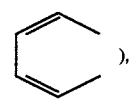), it is also possible to isolate complexes in which the molar ratio of acceptor to donor is 1:2.

In the crystalline state, the complexes according to the invention possess electrical conductivity and accordingly can be used as electrical semiconductors and photoconductors, for example for the antistatic treatment of plastics, as an electrode or storage material in electrical batteries, for the production of solar cells, in fuel cells, for the conversion of radiation and for the production of electronic components.

Suitable radicals $R^1$, $R^2$, $R^3$ and $R^4$ in (I) are those stated above.

Specific examples are the following: $R^1$, $R^2$, $R^3$ and $R^4$ are identical and are each hydrogen, chlorine, methyl or methoxy, or $R^1$ is chlorine, bromine, methyl, ethyl, methoxy, ethoxy, phenyl or tert.-butyl, and $R^2$, $R^3$ and $R^4$ are each hydrogen, or $R^1$ and $R^2$ are identical and are each chlorine, methyl or methoxy and $R^3$ and $R^4$ are each hydrogen, or $R^1$ and $R^3$ are identical and are each chlorine, methyl, methoxy or phenyl and $R^2$ and $R^4$ are each hydrogen, or $R^1$ and $R^4$ are identical and are each chlorine, bromine, methyl, ethyl, methoxy, phenyl or tert.-butyl and $R^2$ and $R^3$ are each hydrogen, or $R^1$, $R^2$ and $R^3$ are each methyl and $R^4$ is a hydrogen, or $R^1$ and $R^2$ together form a radical of the formula

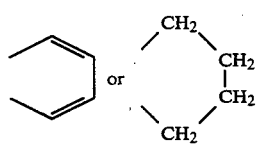

where the fused-on aromatic ring is unsubstituted or monosubstituted or disubstituted by chlorine and/or methyl, and $R^3$ and/or $R^4$ are hydrogen, chlorine or methyl, or $R^1$ and $R^2$ on the one hand and $R^3$ and $R^4$ on the other hand together form a radical of the formula and where the fused-on aromatic rings are unsubstituted or monosubstituted or disubstituted by chlorine and/or methyl.

The fulvalene derivatives of the formula II are known (Synthesis 1976, page 489 et seq.).

Preferred fulvalene derivatives are those of the formula II where X and Y are each S.

Particularly preferred compounds are those thiofulvalene derivatives in which $R^5$, $R^6$, $R^7$ and $R^8$ are identical and are each hydrogen, methyl or phenyl, or $R^5$ is methyl or phenyl, $R^6$ and $R^7$ are each hydrogen and $R^8$ is hydrogen, methyl or phenyl, or $R^5$ and $R^6$ on the one hand and $R^7$ and $R^8$ on the other hand together form a

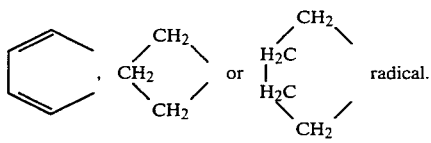

radical.

To prepare the novel 1:1 charge transfer complexes, a biscyanimine of the formula I is reacted with a fulvalene of the formula II in a molar ratio of from 1:1 to 1:2, in a solvent, if appropriate at elevated temperatures. Examples of suitable solvents are dichloromethane, chloroform, 1,1,1-trichloroethane, acetonitrile, benzene, toluene, chlorobenzene and dichlorobenzene.

The charge transfer complexes are isolated in a conventional manner by filtering them off under suction.

In principle, the biscyanimines (I) can be prepared by 2 methods:

(a) by oxidation of an N,N'-dicyano-p-phenylenediamine (III)

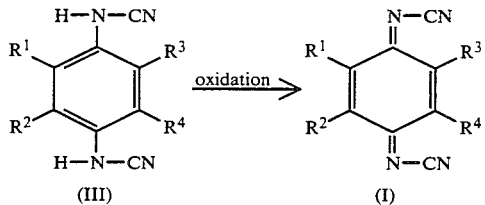

or (b) by reaction of a quinone of the formula IV with bistrimethylsilylcarbodiimide (V)

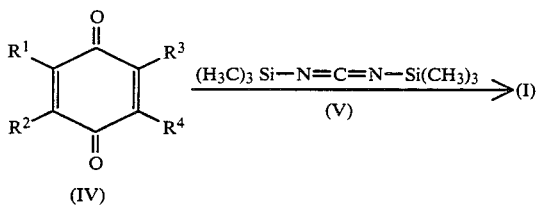

in the presence of a catalyst.

Process (a) has the disadvantage that it cannot be used in every case and that the biscyanamines (III) required as starting materials are difficult to obtain in many cases. Moreover, the oxidation gives, as a rule, a number of by-products which can be separated off only by means of purification operations involving large losses.

The novel biscyanimines (I) are preferably prepared by process (b), which gives (I) in satisfactory purity.

In the reaction of (IV) with (V), not less than 2, preferably from 2.2 to 3, moles of (V) are employed per mole of (IV). Advantageously, the reaction is carried out in an inert organic solvent, eg. dichloromethane, chloroform, 1,1,1-trichloroethane, 1,2-dichloroethane or acetonitrile, and in the presence of a catalyst. Examples of suitable catalysts are cesium fluoride, potassium cyanide/crown ethers, such as 18-crown-6, and titanium tetrachloride. The last-mentioned compound is the preferred catalyst.

The Examples which follow illustrate the invention. Percentages for the yields are percentages of theoretical yield, and DDQ is dichlorodicyano-p-benzoquinone.

EXAMPLE 1

634 mg (4.00 millimoles) of N,N'-biscyano-p-phenylenediamine and 2.86 g (12.0 millimoles) of freshly prepared lead dioxide in 100 ml of absolute benzene are refluxed for 20 minutes, the mixture is filtered under suction, and the orange filtrate is evaporated down to about 10 ml. 50 ml of methylcyclohexane are added, whereupon a flocculent yellow precipitate separates out. The product is filtered off under suction, and 136 mg of N,N'-dicyano-p-benzoquinone bisimine are obtained. The mother liquor is evaporated down, and a further 30 mg of product are precipitated with methylcyclohexane. Total yield: 27% of theory.

EXAMPLE 2

634 mg (4.00 millimoles) of N,N'-biscyano-p-phenylenediamine and 2.27 g (10.0 millimoles) of DDQ in 40 ml of absolute benzene are refluxed for 22 hours, and the mixture is allowed to cool and then evaporated down to about 10 ml. 2.34 g of an orange-yellow product are precipitated with 60 ml of petroleum ether (bp. 40°/60° C.). Further concentration of the mother liquor and precipitation give another 106 mg of product. 1.14 g of the product are chromatographed over a 6×25 cm column filled with 0.063-0.200 silica gel from Woelm, methylene chloride being used as the mobile phase. The yellow eluate is evaporated down to about 5 ml, and 255 mg (87%) of a product of melting point 160°–162° C. (decomposition) are precipitated with 50 ml of 40/60 petroleum ether.

100 mg of product are sublimed at 90° C. under $4 \times 10^{-2}$ mm Hg. 88 mg (70%) of N,N'-dicyano-p-benzoquinone bisimine of melting point 160°–163° C. (decomposition) are obtained.

IR (KBr): 3060 (CH), 2175 (C≡N), 1565 (C=N), 154 cm$^{-1}$ (C=C).-

UV (acetonitrile): $\lambda_{max}$ (lg$\epsilon$)=313 sh (4.35), 330 (4.47), 342 (4.45), 361 nm sh (4.24).-$^1$H-NMR(CH$_3$CN): $\delta$=7.40 ppm (mc, 4H).-$^{13}$C-NMR (CDCl$_3$): $\epsilon$=112.88 (C≡N), 128.53, 129.96, 137.81, 138.66, 174.37 (C=N), 174.52 ppm (C=N).-MS (70 eV): m/e=156 (100%, M+).

EXAMPLE 3

186 mg of crude N,N'-dicyano-2,5-dimethyl-p-phenylenediamine are added to a solution of 227 mg (1.00 millimole) of DDQ in 10 ml of absolute benzene, the mixture is refluxed for 4 hours in the absence of moisture and then filtered off under suction, and the filtrate is evaporated down to about 5 ml. 60 mg (33%) of a yellow solid are precipitated with 25 ml of petroleum ether (bp. 40°/60° C.). Recrystallization from 3 ml of absolute acetonitrile gives 54 mg (30% of theory) of N,N'-dicyano-2,5-dimethyl-p-benzoquinone bisimine in the form of yellow platelets of melting point 320°–321° C.

$C_{10}H_8N_4$ (184.2) Calculated C 65.20 H 4.38 N 30.42 Found C 65.45 H 4.18 N 29.80

IR (KBr): 3050 (CH), 2180 (C≡N), 1590 (C=N), 1535 cm$^{-1}$ (C=C).-UV (acetonitrile): $\lambda_{max}$ (lg$\epsilon$)=330 sh (4.45), 344 (4.49), 363 nm sh (4.31).-$^1$H-NMR (CDCl$_3$/TMS): $\delta$=2.25 (d, J=1 Hz; 6H, CH$_3$), 7.32 ppm (q, J=1 Hz; 2H, -C=C-H).-$^{13}$C-NMR (CDCl$_3$/TMS): $\delta$=16.81 (-CH$_3$), 113.32 (-C≡N), 128.05 (-C-H), 146.64 (C-CH$_3$), 175.93 ppm (C=N).-MS (70 eV): m/e=184 (100%, M$^+$), 157 (78%, M$_+$-HCN).

General method (GM1) for the preparation of N,N'-biscyanoquinone imines (I) by reaction of the p-quinone (IV) with (V).

2.00 millimoles of TiCl$_4$ are added to a solution of 2.00 millimoles of the quinone in 6 ml of CH$_2$Cl$_2$. During this procedure, a yellow or orange precipitate is formed. 4.40 millimoles of (V) in 6 ml of CH$_2$Cl$_2$ are then rapidly added dropwise, and the mixture is stirred while the precipitate dissolves. The course of the reaction is monitored by means of thin layer chromatography (precoated 40×80 mm silica gel plate from Machery, Nagel & Co., methylene chloride as mobile phase). When the reaction is complete, the reaction mixture is filtered via an Alihn tube half filled with a suspension of silica gel (0.063–0.200 from Woelm) in CH$_2$Cl$_2$. The tube is washed with methylene chloride until the eluate no longer has a yellow coloration. The eluate is then evaporated down in a rotary evaporator, and the products are sublimed and/or recrystallized.

EXAMPLE 4

Using method GM1, a solution of 820 mg (4.40 millimoles) of (V) in 6 ml of CH$_2$Cl$_2$ is added dropwise to 216 mg (2.00 millimoles) of p-benzoquinone and 379 g (2.00 millimoles) of TiCl$_4$ in 6 ml of CH$_2$Cl$_2$. After 15 minutes, the mixture is filtered over SiO$_2$, and 156 mg (50%) of N,N'-dicyano-p-benzoquinone bisimine are precipitated with petroleum ether (30°/75° C.). The product is identical to the N,N'-dicyano-p-benzoquinone bisimine obtained as described in Example 1; mp.: 163° C. (decomposition).

$C_8H_4N_4$ (156) Calculated C 61.53; H 2.58; N 35.88; Found C 61.17; H 2.54; N 35.37.

EXAMPLE 5

Using method GM1, 272 mg (2.00 millimoles) of 2,5-dimethyl-p-benzoquinone, 379 mg (2.00 millimoles) of TiCl$_4$ and 820 mg (4.40 millimoles) of (V) in 12 ml of CH$_2$Cl$_2$ are stirred for 3 hours. The mixture is worked up to give 289 mg (78%) of crude product, which is recrystallized from 10 ml of acetonitrile to give 275 mg (75%) of N,N'-dicyano-2,5-dimethyl-p-benzoquinone bisimine. Its properties correspond to those of the N,N'-dicyano-2,5-dimethyl-p-benzoquinone bisimine obtained as described in Example 3; mp.: 320° C. (decomposition).

EXAMPLE 6

885 mg (5.00 millimoles) of 2,5-dichloro-p-benzoquinone, 948 mg (5.00 millimoles) of TiCl$_4$ and 2.05 g (11.0 millimoles) of (V) in 15 ml of CH$_2$Cl$_2$ are reacted by general method GM1. After 3 hours, the mixture is worked up to give 486 mg (43%) of crude product of melting point 195° C. (decomposition), which is sublimed (10$^{-2}$ mm Hg/165° C.) to give 338 mg (30%) of N,N'-dicyano-2,5-dichloro-p-benzoquinone bisimine of melting point 225° C. (decomposition). $C_8H_2Cl_2N_4$ (225.0)

Calculated C 42.70; H 0.90; N 24.90; Cl 31.5; Found C 42.31; H 0.89; N 24.93; Cl 31.5.

IR (KBr): 3039 (CH), 2191 (C≡N), 1673 (C=N), 1651 (C=C), 1255, 1050, 920, 825, 678 cm$^{-1}$.-UV (CH$_2$-CN): $\lambda_{max}$ (lg$\epsilon$)=366 sh (4.25), 347 (4.40), 254 (3.37) nm.-$^1$H-NMR (CDCl$_3$/TMS): $\delta$=7.73 ppm (s, 2H).-$^{13}$C-NMR (CDCl$_3$/TMS): $\delta$=112.26 (C≡N), 128.18 (C-H), 145.47 (C-Cl), 169.27 ppm (C=N).-MS (70 eV): m/e=224 (100%, +).

EXAMPLE 7

Using method GM1, 285 mg (2.00 millimoles) of 2-chloro-p-benzoquinone, 379 mg (2.00 millimoles) of TiCl$_4$ and 820 mg (4.40 millimoles) of (V) in 12 ml of CH$_2$Cl$_2$ are reacted, and the mixture is worked up. After a reaction time of 3 hours, 136 mg (37%) of crude product are obtained. After sublimation (10$^{-2}$ mm Hg/140° C.), N,N'-dicyano-2-chloro-p-benzoquinone bisimine of melting point 158° C. (decomposition) is obtained in 19% yield. IR (KBr): 3041 (CH), 2191 (C≡N), 1670 (C=N), 1655 cm$^{-1}$ (C=C).-$^1$H-NMR (CDCl$_3$/TMS): $\delta$=7.40–7.83 ppm (m).-MS (70 eV): m/e=190 (100%, M$^+$), 155 (10%, M$^+$-Cl), 138 (42%, M$^+$-2CN).

EXAMPLE 8

791 mg (5.00 millimoles) of 1,4-naphthoquinone, 2.05 g (11.0 millimoles) of (V) and 947 mg (5.00 millimoles) of TiCl$_4$ in 30 ml of CH$_2$Cl$_2$ are reacted with one another by general method GM1. After 7 hours, the mixture is worked up to give 362 mg (36%) of crude product. Sublimation under reduced pressure from an oil pump at 160° C. gives N,N'-dicyano-1,4-naphthoquinone bisimine in 29% yield.

$C_{12}H_6N_4$ (206.6) Calculated C 69.75; H 2.93; N 27.12; Found C 70.16; H 3.04; N 27.10.

IR (KBr): 3059 (CH), 2180 (C≡N), 1563 (C=C arom.), 1551 (C=N), 1527 (C=C), 1355, 1195, 1111, 883, 774 cm$^{-1}$.-UV (CH$_3$CN): $\lambda_{max}$ (lg$\epsilon$)=399 (4.00), 344 sh (4.20), 3.29 (4.30), 278 (4.14), 269 (4.15); 253 nm sh (4.01).-$^1$H-NMR (CDCl$_3$/TMS): $\delta$=7.65 (s, 2H, olefin. H), 7.88 (m, 2H, H$_A$), 8.44 ppm (m, 2H, H$_B$).-$^{13}$C-NMR (CDCl$_3$/TMS): $\delta$=113.15 (C-1), 126.47 (C-2), 130.03 (C-3), 131.29 (C-4), 134.93 (C-5), 175.45 ppm (C-6).-MS (70 eV): m/e=206 (100%, M$^+$), 179 (21%, M$^+$+HCN), 165 (7% M$^+$-HNCN), 154 (34%, M$^+$-2CN), 128 (45%, M$^+$-3CN), 102 (12%, M$^+$-4CN), 101 (15%, M$^+$-3CN-HCN), 76 (12%, M$^+$-4CN-C$_2$H$_4$).

EXAMPLE 9

Using method GM1, 554 mg (2.00 millimoles) of 1,5-dichloroanthraquinone, 379 mg (2.00 millimoles) of TiCl$_4$ and 820 mg (4.40 millimoles) of (V) are stirred for 31 hours. Working up gives 511 mg of a mixture, which is subjected to flash chromatography (0.032–0.063 silica gel from Woelm, methylene chloride). Three fractions are obtained:

Fraction 1: 112 mg (20%) of 1,5-dichloroanthraquinone (IR)

Fraction 2: 73 mg (12%) of N-cyano-2,5-dichloro-9,10-anthraquinone monoimine

Fraction 3: 135 mg (21%) of N,N'-dicyano-1,5-dichloro-9,10-anthraquinone bisimine.

After recrystallization from acetonitrile, 17% of N,N'-dicyano-1,5-dichloro-9,10-anthraquinone bisimine of melting point 313°–315° C. is isolated. IR (KBr): 3070

(CH), 2180 (C≡N), 1599 (C=C), 1562 cm$^{-1}$ (C=N).-UV (CH$_3$CN): $\lambda_{max}$ (lgε)=363 sh (3.35), 306 (4.17), 275 nm (4.94).-MS 70 eV): m/e=324 (35%, M+), 289 (100%, M+-Cl).

EXAMPLE 10

Reaction of p-benzoquinone with (V) and TiCl$_4$ (inverse reaction procedure to method GM1.

216 mg (2.00 millimoles) of p-benzoquinone and 820 mg (4.40 millimoles) of (V) in 6 ml of CH$_2$Cl$_2$ are initially taken, and 379 mg (2.00 millimoles) of TiCl$_4$ in 6 ml of CH$_2$Cl$_2$ are added dropwise in the course of 10 minutes. The mixture is stirred for 10 minutes, and is worked up as described in Example 4. 81 mg (26%) of N,N'-dicyano-p-benzoquinone bisimine are isolated.

EXAMPLE 11

416 mg (2.00 millimoles) of 9,10-anthraquinone, 820 mg (4.40 millimoles) of (V) and 61 mg (0.40 millimole) of CsF in 20 ml of acetonitrile are stirred for 22 hours, the volatile components are stripped off, the brown reaction product is extracted with benzene, and the solvent is stripped off to give 341 mg (67%) of yellow crystals. After recrystallization from 8 ml of acetonitrile, 319 mg (62%) of N,N'-dicyano-9,10-anthraquinone bisimine of melting point 225°-226° C. are isolated. IR (KBr): 3079 (CH), 2171 (C≡N), 1611 (C=C), 1599 (C=C), 1564 cm$^{-1}$ (C=N).-UV (CH$_3$CN): $\lambda_{max}$ (lgε)=332 (4.36), 251 nm (4.54).-$^1$H-NMR (60 MHz, CDCl$_3$/TMS): δ=7.74-8.04 (m, 4H, H$_A$), 8.57-9.07 ppm (m, 4H, H$_B$).-$^{13}$C-NMR (CDCl$_3$/TMS): δ=113.68 ($\underline{C}$-1), 127.81 ($\underline{C}$-2), 131.68 ($\underline{C}$-3), 134.79 ($\underline{C}$-4), 171.70 ppm ($\underline{C}$-5).-MS (70 eV): m/e=256 (100%, M+), 230 (14%, M+-CN), 229 (13%, M+-HCN), 215 (10%, M+NHCN), 202 (15%, M+-2HCN).

EXAMPLE 12

N,N'-Dicyano-2,5-dibromo-p-benzoquinone bisimine 3.79 g (20.0 millimoles) of titanium tetrachloride are added to a solution of 2.66 g (10.0 millimoles) of 2,5-dibromo-p-benzoquinone in 100 ml of dichloromethane. 4.66 g (25.0 millimoles) of bistrimethylsilylcarbodiimide in 30 ml of dichloromethane are added dropwise, during which a dark precipitate separates out from the red solution. The mixture is stirred for 5.5 hours and then poured onto 250 ml of petroleum ether (bp. 39/59° C.), and 6.33 g of dark solid are filtered off under suction. This is extracted with 50 ml of hot benzene, and 680 mg (22%) of N,N'-dicyano-2,5-dibromo-p-benzoquinone bisimine of melting point 239° C. (decomposition) are precipitated with 50 moles of petroleum ether (bp. 30/75° C.). Sublimation under reduced pressure from an oil pump at 130° C./4×10$^{-5}$ mm Hg gives 228 mg (7%) of N,N'-dicyano-2,5-dibromo-p-benzoquinone bisimine having the same melting point. IR (KBr): 3043 (C-H), 2179 (C≡N), 1570 (C=N), 1554 (C=C), −1244, 1024, 896, 808, 696 cm$^{-1}$.-UV (CH$_3$CN): $\lambda_{max}$ (lgε)=264 sh (3.65, 331 sh (4.40), 346 sh (4.56), 348 (4.47), 365 sh nm (4.43).-$^1$H-NMR (CDCl$_3$/TMS): δ=8.07 ppm (s, 2H).-$^{13}$C-NMR (CDCl$_3$/TMS): δ=112.42 (C≡N), 132.23 ppm (=C-H).-MS (70 eV): m/e=313 (M+, 100%), 233 (M+-Br, 37%).

EXAMPLE 13

N,N'-Dicyano-2,5-dimethoxy-p-benzoquinone bisimine 1.90 g (10.0 millimoles) of titanium tetrachloride are added to a solution of 681 mg (5.00 millimoles) of 2,5-dimethoxy-p-benzoquinone in 50 ml of dichloromethane, a brown precipitate separating out during this procedure. This precipitates redissolves when 4.19 g (22.5 millimoles) of (V) in 20 ml of dichloromethane are added. The solution is stirred for 3 hours and then poured into 250 ml of petroleum ether (bp. 30/75° C.), the pale brown precipitate is filtered off under suction and suspended in 70 ml of benzene, and the suspension is heated gently and filtered. The benzene phase is evaporated down to about 20 ml, and 671 mg of an orange solid are precipitated with 50 ml of petroleum ether. 600 mg of still moist product are recrystallized from 65 ml of xylene, the solution being filtered while hot. Drying over silica gel gives 143 mg (13%) of pure N,N'-dicyano-2,5-dimethoxy-p-benzoquinone bisimine, which sublimes above 190° C. and decomposes above 265° C.

C$_{10}$H$_8$N$_4$O$_2$ (216.2) Calculated C 55.55; H 3.73; N 25.92; Found C 55.15; H 3.62; N 26.08. IR (KBr): 3036 (C-H), 3007 (C-H), 2954 (C-H), 2179 (C≡N), 1589 (C=C), 1569 (C=N), 1312, 1239, 1002, 818 cm$^{-1}$.-UV (CH$_3$CN): $\lambda_{max}$ (lgε)=260 (3.69), 302 sh (3.57), 360 (4.50), 382 sh nm (4.33).-$^1$H-NMR (CDCl$_3$/TMS) δ=4.03 (s, 6H, OCH$_3$), 6.54 ppm (s, 2H, =C-H).-$^{13}$C-NMR (CDCl$_3$/TMS) δ=57.76 ($\underline{C}$-9.10), 102.03 ($\underline{C}$-3.6), 113.38 ($\underline{C}$-7.8), 162.10 ($\underline{C}$-2.5), 170.20 ppm ($\underline{C}$-1.4).-MS (70 eV): m/e=216 (M+, 60%), 161 (M+-CH$_3$-NCN, 77%), 93 (100%).-

EXAMPLE 14

N,N'-Dicyano-2,5-di-tert.-butyl-p-benzoquinone bisimine 759 mg (4.00 millimoles) of titanium tetrachloride are added to a solution of 441 mg (2.00 millimoles) of 2,5-di-tert.-butyl-p-benzoquinone in 50 ml of dichloromethane, and 1.68 g (9.00 millimoles) of (V) in 20 ml of dichloromethane are added dropwise. After 5 days, the mixture is diluted with 250 ml of dichloromethane, stirred for 5 minutes with a pinch of powdered active carbon and then filtered, the filtrate is evaporated down to about 5 ml, and 267 mg of an orange solid of melting point 213°-240° C. are precipitated with 100 ml of petroleum ether (bp. 30/75° C.). This solid is recrystallized from 10 ml of methylcyclohexane, the solution being filtered while hot. 54 mg (10%) of pure N,N'-dicyano-2,5-di-tert.-butyl-p-benzoquinone bisimine, which has a melting point of 241° C. and sublimes above 200° C., are obtained.

C$_{16}$H$_{20}$N$_4$ (268.4) Calculated C 71.61; H 7.51; N 20.88; Found C 71.40; H 7.60; N 20.99. IR (KBr): 3002 (C-H), 2971 (C-H), 2910 (C-H), 2871 (C-H), 2181 (C≡N), 1581 (C=C), 1544 (C=N), 1318, 1228, 1092, 903 cm$^{-1}$.-UV (CH$_3$CN): $\lambda_{max}$(lgε)=343 (4.46), 367 sh nm (4.25).-$^1$H-NMR (CDCl$_3$/TMS): δ=1.39 (s, 18H, t-Bu-H), 7.38 pp (s, 2H, ring-H).-$^{13}$C-NMR (CDCl$_3$/TMS): δ=29.98 ($\underline{C}$-11-16), 36.27 ($\underline{C}$-9.10), 112.64 ($\underline{C}$-7.8), 128.43 ($\underline{C}$-3.6), 154.89 ($\underline{C}$-2.5), 175.85 ppm ($\underline{C}$-1.4).-MS (70 eV): m/e=270 (M+ +2H, 16%), 268 (M+, 71%), 253 (M+-CH$_3$, 100%), 238 (M+-2CH$_3$, 18%), 228 (M+-NCN, 40%), 226 (M+-2CN, 28%), 212 (M+-2CH$_3$-CN, 50%), 211 (M+-2CH$_3$-HCN, 34%), 201 (M+-NCN-HCN, 25%), 200 (M+-HNCN-HCN, 30%), 199 (M+-H$_2$NCN-HCN, 25%), 185 (M+-t-Bu-Cn, 41%), 172 (M+-2CH$_3$-NCH-CN, 44%).

EXAMPLE 15

N,N'-Dicyano-2,5-diphenyl-p-benzoquinone bisimine 759 mg (4.00 millimoles) of titanium tetrachloride and, thereafter, a solution of 1.49 g (8.00 millimoles) of (V) in 10 ml of dichloromethane are added to a solution of 520 mg (2.00 millimoles) of 2,5-diphenyl-p-benzoquinone in 50 ml of dichloromethane. The mixture is stirred for 8 hours, filtered over 0.062–0.200 silica gel from Woelm and then evaporated down in a rotary evaporator to give 440 mg (71%) of a red solid of melting point 305° C. (decomposition). 424 mg of product are recrystallized from 10 ml of toluene, and 332 mg (54%) of pure N,N'-dicyano-2,5-diphenyl-p-benzoquinone bisimine are obtained in the form of orange crystals of melting point 311° C. (decomposition).

IR (KBr): 2173 (C≡N), 1581 (C-C), 1561 (C=C), 1540 (C=N), 1444, 1223, 894, 720, 705 cm$^{-1}$.-UV (CH$_3$CN): $\lambda_{max}$ (lg$\epsilon$)=237 (4.31), 340 (4.30), 387 sh nm (3.95).-$^1$H-NMR (CDCl$_3$/TMS): $\delta$=7.47 (s, 10H, aromatic-H), 7.52 ppm (s, 2H, quinone-H).-$^{13}$C-NMR (CDCl$_3$/TMS): $\delta$=113.32 (C-7.8), 127.90 (C-3.6), 128.76 (C-4'), 130.07 (C-3'), 131.00 (C-2'), 132.24 (C-1'), 147.66 (C-2.5), 175.25 (C-1.4).-MS (70 eV): m/e=308 (M+, 100%), 282 (M+-CN, 10%), 281 (M+-HCN, 25%), 280 (M+-H$_2$CN, 57%), 268 (M+-NCN, 13%), 266 (M+-H$_2$NCN, 10%).

EXAMPLE 16

N,N'-Dicyano-2,6-dimethyl-p-benzoquinone bisimine 759 mg (4.00 millimoles) of titanium tetrachloride are added to 272 mg (2.00 millimoles) of 2,6-dimethyl-p-benzoquinone in 40 ml of dichloromethane. 1.68 g (9.00 millimoles) of (V) in 20 ml of dichloromethane are added dropwise, a precipitate separating out from the red solution during this procedure. The mixture is stirred for 9 hours, after which it is filtered over 0.062–2.00 silica gel from Woelm, and the filtrate is evaporated down in a rotary evaporator to give 269 mg of a product of melting point 70°–110° C. This product is recrystallized from 16 ml of cyclohexane, the solution being filtered while hot, and 57 mg (15%) of N,N'-dicyano-2,5-dimethyl-p-benzoquinone bisimine are obtained in the form of yellow crystals of melting point 116°–119° C.

C$_{10}$H$_8$N$_4$ (184.2) Calculated C 65.20; H 4.38; N 30.42; Found C 64.84; H 4.43; N 30.40. IR (KBr): 3040 (C-H), 2962 (C-H), 2168 (C≡N), 1587 (C=C), 1563 (C=N).-UV (CH$_3$CN): $\lambda_{max}$ (lg$\epsilon$)=332 sh (4.40), 338 (4.51), 351 (4.47), 380 sh nm (3.45).-$^1$H-NMR (CDCl$_3$/TMS): $\delta$=2.43 (broad s, 6H, CH$_3$), 6.96 (broad s, 1H, anti-H), 724 (broad s, 1H, syn-H).-$^{13}$C-NMR (CDCl$_3$/TMS): $\delta$=19.38 (C-9), 19.53 (C-10), 112.86 (C-8), 113.59 (C-7), 126.98 (C-3), 135.44 (C-5), 173.19 (C-4), 174.52 (C-1); C-2 and C-6 cannot be detected because of excessive broadening of the signal.

EXAMPLE 17

1.90 g (10.0 millimoles) of titanium tetrachloride are added to a solution of 596 mg (4.00 millimoles) of trimethyl-p-benzoquinone in 50 ml of dichloromethane. 4.20 g (32.5 millimoles) of (V) in 20 ml of dichloromethane are added dropwise to the resulting red solution, the mixture is stirred for 7 hours and then run into 400 ml of petroleum ether (30/75° C.), the resulting mixture is filtered under suction, and the mother liquor is evaporated down in a rotary evaporator to give 2.15 g of an oily orange solid. This is recrystallized from 14 ml of methylcyclohexane to give 151 mg (19%) of N,N'-dicyano-2,3,5-trimethyl-p-benzoquinone bisimine in the form of yellow crystals of melting point 120° C. (decomposition). This product is stirred in 30 ml of carbon tetrachloride, the solution is filtered and the filtrate is evaporated down in a rotary evaporator. 118 mg (15%) of N,N'-dicyano-2,3,5-trimethyl-p-benzoquinone bisimine of melting point 122° C. are isolated. IR (KBr): 2178 (CN), 2158 (C≡N), 1633 (C=C), 1556 (C=N), 1382 cm$^{-1}$.-UV (CH$_3$CN): $\lambda_{max}$ (lg$\epsilon$)=324 sh (4.36), 341 (4.46), 355 sh nm (4.40).-$^1$H-NMR (CDCl$_3$/TMS): $\delta$=2.28 (s, 3H, H$_A$), 2.40 (s, 3H, H$_B$), 2.48 (s, 3H, H$_C$), 7.32 ppm (s, 1H, H$_D$).-$^{13}$C-NMR (CDCl$_3$/TMS): $\delta$=15.59 (C-10), 16.00 (C-9), 19.41 (C-11), 113.01 (C-7), 113.65 (C-8), 127.06 (C-6), 142.12 (broad, weak, C$_{3,5}$), 173.32 (C-4), 175.05 (C-1).-MS (70 eV): m/e=200 (M++2H, 13%), 198 (M+, 39%), 174 (M++2H-CN, 100%), 170 (M++2H-2CH$_3$, 17%), 146 (M+-2CH, 81%), 145 (M+-CN-HCN, 87%), 132 (M+-2CN-CH$_3$).

EXAMPLE 18

759 mg (4.00 millimoles) of titanium tetrachloride are added to a solution of 328 mg (2.00 millimoles) of tetramethyl-p-benzoquinone in 50 ml of dichloromethane, and the mixture is stirred until a yellow precipitate appears, which takes 5 minutes. 1.68 g (9.00 millimoles) of (V) in 20 ml of dichloromethane are then slowly added dropwise, and stirring is continued for 19 hours. Thereafter, the reaction mixture is filtered through 0.062–0.200 silica gel from Woelm, the solvent is evaporated off in a rotary evaporator, and 223 mg (53%) of crude product of melting point 110°–123° C. (decomposition) are obtained. 84 mg of product are recrystallized from 5 ml of cyclohexane, and 78 mg (49%) of N,N'-dicyanotetramethyl-p-benzoquinone-bisimide of melting point 125°–127° C. (decomposition) are isolated as long orange needles.

C$_{12}$H$_{12}$N$_4$ (212.2) Calculated C 67.95; H 5.70; N 26.40; Found C 67.65; H 5.67; N 26.18.

IR (KBr): 2149 (C≡N), 1576 (C=C), 1560 (C=N), 1381, 678 cm$^{-1}$.-UV (CH$_3$CN): $\lambda_{max}$ (lg$\epsilon$)=331 sh (3.87), 346 (4.37), 368 sh nm (4.15).-$^1$H-NMR (CDCl$_3$/TMS): $\delta$=2.37 ppm (s, 12H, CH$_3$).-$^{13}$C-NMR (CDCl$_3$/TMS): $\delta$=15.50 (CH$_3$), 113.25 (C=N), 138.98 (C-CH$_3$), 173.99 ppm (C=N).-MS (70 eV): m/e=212 (M+, 100%), 185 (M+-HCN, 28%), 170 (M+-HCN-CH$_3$, 30%), 160 (M+-2CN, 92%), 159 (M+-HCN-CN, 35%), 158 (M+-3HCN, 26%), 145 (M+-2CN-2CH$_3$, 65%).

EXAMPLE 19

759 mg (4.00 millimoles) of titanium tetrachloride are added to 456 mg (2.00 millimoles) of tetramethoxy-p-benzoquinone in 50 ml of dichloromethane, and 168 g (9.00 millimoles) of bistrimethylsilylcarbodiimide in 10 ml of dichloromethane are added dropwise to the resulting black solution. The mixture is stirred for 8 hours, after which it is diluted with 250 ml of dichloromethane, stirred for 5 minutes with a large pinch of powdered active carbon, filtered and then evaporated down to about 20 ml, and 516 mg (93%) of a solid of melting point 153°–175° C. are precipitated with 200 ml of petroleum ether (30/75° C.). This solid is recrystallized from 20 ml of benzene, the solution being filtered while hot, and 256 mg of needles of melting point 172°–173° C. are obtained. A further 75 mg of product of the same melting point are precipitated from the mother liquor with 50 ml of petroleum ether (30/75° C.). The total yield is 59% of N,N'-dicyanotetramethoxy-p-benzoquinone bisimine.

$C_{12}H_{12}N_4O_4$ (276.2) Calculated C 52.17; H 4.38; N 20.29; Found C 51.92; H 4.09; N 20.04. IR (KBr): 2951 (C-H), 2948 (C-H), 2160 (C≡N), 1592 (C=C), 1554 (C=N), 1458, 1442, 1198, 1083, 998, 910, 854, 727, 697, 653 cm$^{-1}$.-UV (CH$_3$CN): $\lambda_{max}$ (lgϵ)=356 sh (4.48), 368 nm (4.54).-$^1$HNMR (CDCl$_3$/TMS): δ=4.03 ppm (broad s, 12H, OCH$_3$).-$^{13}$C-NMR (CDCl$_3$/TMS): δ=62.02 (OCH$_3$), 62.08 (OCH$_3$), 112.89 (C≡N), 144.26 (C-OCH$_3$), 166.52 ppm (C=N).-MS (70 eV): m/e=292, 276 (M$^+$, 100%), 261 ($\overline{M}^+$-CH$_3$, 60%).

EXAMPLE 20

12.1 g (64.8 millimoles) of titanium tetrachloride are added to 492 mg (2.00 millimoles) of chloranil in 50 ml of dichloromethane, and 9.32 g (50.0 millimoles) of (V) in 20 ml of dichloromethane are added dropwise to the resulting dark yellow suspension. The precipitate disappears, the solution becomes red and then changes to black, and orange-red crystals are precipitated from the black solution after some time. The mixture is stirred for 30 hours, after which the precipitate is filtered off under suction and extracted with hot benzene. The solvent is evaporated down to 10 ml, and 359 mg (61%) of orange-red crystals of melting point 252°–255° C. (decomposition) are precipitated with 50 ml of petroleum ether (30/75° C.).

324 mg of product are recrystallized from 20 ml of acetonitrile, and 140 mg (26%) of N,N'-dicyanotetrachloro-p-benzoquinone bisimine are isolated as orange crystals of melting point 258° C. (decomposition).

$C_8Cl_4N_4$ (293.9) Calculated C 32.69; N 19.07; Found C 32.33; N 19.04.

IR (KBr): 2178 (C≡N), 2155 (C≡N), 1576 (C=C), 1516 (C=N), 1160, 1146, 1133, 1090, 842, 738 (C-Cl), 680 cm$^{-1}$.-UV (CH$_3$CN): $\lambda_{max}$ (lgϵ)=309 sh (3.75), 327 sh (4.20), 344 sh (4.47), 353 (4.48), 361 sh (4.51), 366 (4.52), 372 sh nm (4.45).-MS (70 eV): m/e=292 (M$^+$, 45%), 257 (M$^+$-Cl, 20%), 240 (M$^+$-2CN, 58%), 205 (M$^+$-Cl-2CN, 23%), 111 (M$^+$—Cl—C$_2$Cl$_2$—2CN, 100%).

N,N'-Dicyanoquinone bisimines of the formula (I) are prepared by the general method (GM2) below.

Titanium tetrachloride is added to a solution of the quinone (IV) in dichloromethane in the absence of moisture, and, as a rule, a yellow or orange precipitate separates out. Bistrimethylsilylcarbodiimide (V) in a little dichloromethane is rapidly added dropwise, the dark reaction mixture is stirred at room temperature and the poured onto ice water, the organic phase is separated off and dried over anhydrous magnesium sulfate, and the organic solution is evaporated down in a rotary evaporator until the first crystals are precipitated. Precipitation is completed by adding petroleum ether (30/75° C.). The crystals are then recrystallized from the solvent stated in the table below. The biscyanoquinone imines stated in Examples 21 to 34 are prepared by this method. The amounts of (IV), (V), titanium tetrachloride and methylene chloride, the reaction time and the yield of biscyanoquinone bisimine are summarized in the table below. The biscyanoquinone bisimines are characterized by their melting points.

Method GM2 aboves gives the dicyanoquinone bisimines in higher yield and better purity than method GM1.

EXAMPLES 21 TO 34

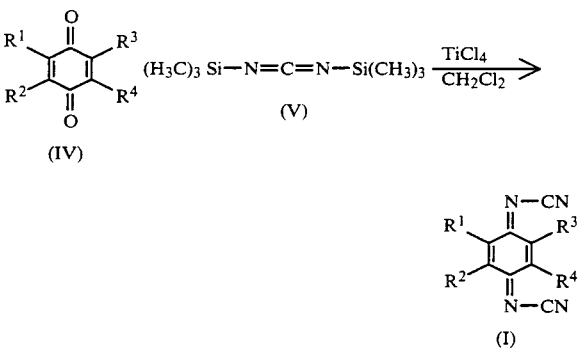

| Example | R$^1$ | R$^2$ | R$^3$ | R$^4$ | IV millimoles | V millimoles | TiCl$_4$ millimoles | CH$_2$Cl$_2$ [ml] | Reaction time [hours] | Yield [%] | Recrystallized from | Mp. [°C.] |
|---|---|---|---|---|---|---|---|---|---|---|---|---|
| 21 | —CH$_3$ | —H | —CH$_3$ | —H | 2 | 12 | 10 | 30 | 1 | 42 | cyclohexane | 125–126 |
| 22 | —CH$_3$ | —CH$_3$ | —H | —H | 10 | 60 | 50 | 40 | 3 | 43 | methylcyclohexane/toluene | 173–175 |
| 23 | —CH$_3$ | —CH$_3$ | —H | —CH$_3$ | 4 | 20 | 15 | 50 | 3 | 35 | methylcyclohexane | 125–126 |
| 24 | —C$_2$H$_5$ | —H | —C$_2$H$_5$ | —H | 2 | 12 | 10 | 30 | 1 | 39 | cyclohexane | 64–64.5 |
| 25 | —C(CH$_3$)$_3$ | —H | —C(CH$_3$)$_3$ | —H | 2 | 25 | 10 | 60 | 26 | 58 | methylcyclohexane | 241 |
| 26 | —OCH$_3$ | —H | —H | —OCH$_3$ | 2 | 12 | 10 | 30 | 1 | 84 | o-dichlorobenzene | 265 |
| 27 | —Cl | —H | —H | —CH$_3$ | 4 | 9 | 8 | 40 | 8 | 42$^a$ | benzene | 179–182 |
| 28 | —Cl | —H | —Cl | —H | 2 | 12 | 10 | 30 | 1 | 25 | methylcyclohexane | 128–130 |
| 29 | —Cl | —CH$_3$ | —CH$_3$ | —Cl | 2 | 25 | 20 | 50 | 2.5 | 52 | acetic acid | >350 |
| 30 | —CH$_3$ | —H | ⌬ | | 2 | 12 | 10 | 40 | 2.5 | 63 | toluene/methylcyclohexane | >35 |
| 31 | —Cl | —H | ⌬ | | 2 | 12 | 10 | 40 | 2 | 63 | acetonitrile | 192 |

-continued

| Example | R¹ | R² | R³ | R⁴ | IV millimoles | V millimoles | TiCl₄ millimoles | CH₂Cl₂ [ml] | Reaction time [hours] | Yield [%] | Recrystallized from | Mp. [°C.] |
|---|---|---|---|---|---|---|---|---|---|---|---|---|
| 32 | ⟨phenyl⟩–CH₃ | | ⟨phenyl⟩ | | 2 | 25 | 10 | 70 | 21 | 28[a] | toluene/methyl-cyclohexane | 166 |
| 33 | ⟨phenyl⟩–CH₃, CH₃ | | ⟨phenyl⟩ | | 2 | 25 | 10 | 70 | 23 | 77 | acetonitrile | 222–223 |
| 34 | OCH₃, ⟨phenyl⟩, OCH₃ | | ⟨phenyl⟩ | | 5 | 30 | 20 | 180 | 3 | 34[a] | DMSO | 329–330 |

[a]The reaction mixture is poured into petroleum ether, the precipitate is filtered off under suction and extracted with hot benzene, the benzene extract is evaporated down, and the dicyanoquinone bisimine is precipitated with petroleum ether.
DMSO = dimethyl sulfoxide.

EXAMPLE 35

A hot solution of 51 mg (0.250 millimole) of tetrathiafulvalene in 5 ml of acetonitrile is poured into a hot solution of 56 mg (0.249 millimole) of N,N'-dicyano-2,5-dichloro-p-benzoquinone bisimine in 5 ml of acetonitrile. The product is filtered off under suction, washed with a little ether and dried to give 105 mg (98%) of a black charge transfer complex having a donor/acceptor ratio of 1:1 and a melting point of 350° C.

$C_{14}H_6Cl_2N_4S_4$ (429.4) Calculated C 39.16; H 1.41; N, 13.05%; Found C 38.88; H 1.13; N 13.05. (KBr): 2122 cm$^{-1}$ (C≡N).

EXAMPLE 36

190 mg (605 μmoles) of N,N'-dicyano-2,5-dibromo-p-benzoquinone bisimine are dissolved in 45 ml of dichloromethane, this solution is filtered into a flask, and a solution of 124 mg (605 μmoles) of tetrathiafulvalene in 10 ml of dichloromethane is added. The dark precipitate which immediately separates out is stirred for 0.5 hour, after which the mixture is filtered under suction and the residue is washed with a little dichloromethane and dried over silica gel to give 283 mg (90%) of the 1:1 charge transfer complex of tetrathiafulvalene and N,N'-dicyano-2,5-dibromo-p-benzoquinone bisimine in the form of a violet solid of melting point 350° C.

$C_{14}H_6Br_2N_4S_4$ (518.3) Calculated C 32.44; H 1.17; N 10.81; Found C 32.60. H 0.96; N 10.89.

IR (KBr): 3088 (C-H), 2122 (C≡N), 1557 (C=C), 1502 (C=N), 1352, 1037 cm$^{-1}$.-UV (CH₃CN): λ$_{max}$ (lgε)=256 (3.64), 290 sh (3.88), 297 (3.92), 349 sh (4.29), 361 sh (4.39), 363 (4.40), 364 sh (3.39), 425 sh (4.17), 430 (4.19), 459 sh (3.87), 464 sh (3.84), 475 sh (3.67), 484 (3.68), 574 (3.97), 605 sh (4.06), 620 sh (4.16), 622 (4.17), 632 sh (4.09), 666 sh (4.00), 686 sh (4.24), 688 nm (4.25).

EXAMPLE 37

(a) A solution of 102 mg (500 μmoles) of tetrathiafulvalene in 10 ml of acetonitrile is added to a hot solution of 103 mg (500 μmoles) of N,N'-dicyano-1,4-naphthoquinone bisimine in 20 ml of acetonitrile. The green solution is refluxed for 2 hours, after which a further 102 mg (500 μmoles) of tetrathiafulvalene are added and half the solvent is stripped off, a black solid crystalling out. The mixture is heated once again until all solid material has dissolved, after which the solution is allowed to cool. The charge transfer complex crystallizes out together with the sparingly soluble bisimine. After 6 days, thin black glossy needles as long as one cm have grown in the solution. These needles are the charge transfer complex of tetrathiafulvalene and N,N'-dicyano-1,4-naphthoquinone bisimine, and are separated off and washed with a little acetonitrile.

(b) A solution of 306 mg (1.50 millimoles) of tetrathiafulvalene in 5 ml of acetonitrile is poured over 103 mg (500 μmoles) of N,N'-dicyano-4,4-naphthoquinone bisimine in a conical flask, and the mixture is left to stand for 30 days in the closed flask. The product is filtered off under suction and dried, and 204 mg (100%) of the microcrystalline 1:1 charge transfer complex of tetrathiafulvalene and N,N'-dicyano-1,4-naphthoquinone bisimine are obtained. This complex decomposes above 163° C.

$C_{18}H_{10}N_4S_4$ (411.0) Calculated C 52.60; H 2.45; N 13.64; S 31.20; Found C 52.55; H 2.32; N 13.47; S 31.02.

UV (CH₃CN): λ$_{max}$ (lgε)=268 sh (5.00), 271 (5.01), 277 (5.03), 317 sh (5.22), 320 (5.23), 349 sh (4.95), 379 sh (4.80), 460 sh (3.79), 480 (3.25), 486 sh (3.24), 354 sh (2.80), 572 (2.72), 590 (2.78), 598 sh (2.72), 645 nm (2.85).

The conductivity measured on isolated crystals was 25 Ω$^{-1}$. cm$^{-1}$.

EXAMPLE 38

A solution of 204 mg (2.00 millimoles) of tetrathiafulvalene in 5 ml of acetonitrile is added to a suspension of 184 mg (1.00 millimole) of N,N'-dicyano-2,5-dimethyl-p-benzoquinone bisimine in 10 ml of acetonitrile at 50° C. The mixture is stirred for 1 hour at this temperature and the warm green solution is filtered and left to stand for 6 hours. During this time, black rods as long as about 2 mm crystallize out. 99 mg (26%) of the charge transfer complex of tetrathiafulvalene and N,N'-dicyano-2,5-dimethyl-p-benzoquinone bisimine of melting point 147° C. (decomposition) are isolated.

$C_{16}H_{12}N_4S_4$ (388.5) Calculated C 49.49; H 3.11; N 14.47; Found C 49.74; H 3.15; N 14.03.

IR (KBr): 2157 (C≡N), 1582 (C=C), 1535 (C=N), 1320, 1278, 1246, 882, 797, 731, 683, 665 cm$^{-1}$.-UV (CH₃CN): λ$_{max}$ (lgε)=300 sh (4.30), 325 (4.50), 342 (4.48), 349 sh (4.44), 362 sh nm (4.24).

EXAMPLE 39

A solution of 55 mg (352 μmoles) of N,N'-dicyano-p-benzoquinone bisimine in 25 ml of absolute acetonitrile is added to a solution of 72 mg (352 μmoles) of tetrathiofulvalene in 25 ml of absolute acetonitrile under N₂. Black needles are precipitated immediately. These are filtered off under suction, washed with absolute acetonitrile and absolute ether and dried over silica gel under 20 mm Hg and at 50° C. 114 mg (90%) of the 1:1 charge transfer complex of N,N'-dicyano-p-benzoquinone bisimine and tetrathiofulvalene are obtained, the complex having a melting point of 350° C.

$C_{14}H_8N_4S_4$ (360.5) Calculated C 46.64; H 2.24; N 15.54; Found C 46.00; H 2.24; N 15.91.

IR (KBr): 2120 cm$^{-1}$ (C≡N).-UV (acetonitrile): $\lambda_{max}$ (lgε)=316 (4.19), 359 (4.29), 509 sh (3.34), 522 sh (3.45), 547 sh (3.67), 559 sh (3.79), 569 (3.84), 584 sh (3.84), 613 (4.07), 678 (4.12), 1903 (3.68), 1940 nm sh (3.02).

Conductivity (crystal powder): δ=6.1 Ω$^{-1}$. cm$^{-1}$.

EXAMPLES 40 TO 43

A warm solution of tetrathiafulvalene (IIa) in anhydrous acetonitrile is added to a solution or suspension of the dicyanoquinone bisimine (Ia) in anhydrous acetonitrile. The molar ratio of (Ia) to (IIa) is 1:1 or 1:2. The crystals formed are filtered off under suction and washed with a little dichloromethane or acetonitrile, and the complex is dried over silica gel at room temperature.

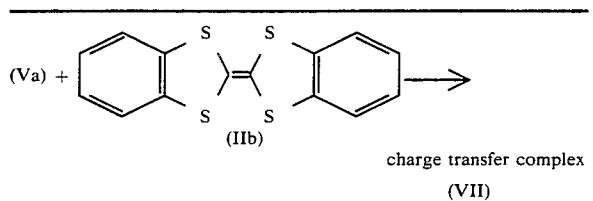

charge transfer complex (VII)

| Example | (Va) R¹ | R⁴ | Yield (% of theory) | Mp. [°C.] | | Analysis C [%] | H [%] | N [%] |
|---|---|---|---|---|---|---|---|---|
| 44 | —H | —H | 37[1] | 140 | calculated | 57.37 | 2.63 | 12.17 |
|  |  |  |  |  | found | 57.39 | 2.45 | 12.19 |
| 45 | —Cl | —Cl | 41[2] | 227 | calculated | 51.85 | 2.18 | 6.72 |
|  |  |  |  |  | found | 51.52 | 2.12 | 6.69 |
| 46 | —Br | —Br | 57[2] | 229 | calculated | 46.85 | 1.97 | 6.07 |
|  |  |  |  |  | found | 46.87 | 1.66 | 6.22 |

[1]1:1 complex
[2]The ratio of acceptor to donor in the complex is 1:2

We claim:
1. A charge transfer complex of a biscyanimine of the formula

(I)

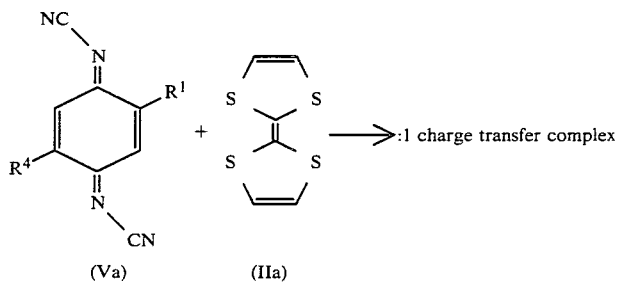

| | (Va) | | Yield | Mp. | | Analysis | | |
|---|---|---|---|---|---|---|---|---|
| Example | R¹ | R⁴ | (% of theory) | [°C.] | | C | H | N |
| 40 | —CH₃ | —H | 75 | 140 | calculated | 48.11 | 2.69 | 14.96 |
|  |  |  |  |  | found | 48.45 | 2.47 | 15.32 |
| 41 | —CH₃ | —Cl | 94 | 144 | calculated | 44.05 | 2.22 | 13.70 |
|  |  |  |  |  | found | 43.80 | 2.21 | 13.71 |
| 42 | —Cl | —H | 87 | 220 | calculated | 42.58 | 1.79 | 14.19 |
|  |  |  |  |  | found | 42.52 | 1.36 | 13.98 |
| 43 | —OCH₃ | —OCH₃ | 56 | 199 | calculated | 45.69 | 2.88 | 13.33 |
|  |  |  |  |  | found | 46.04 | 2.75 | 13.12 |

EXAMPLES 44 TO 46

The procedure described in Examples 40 to 43 is followed, except that tetrathiafulvalene is replaced by the equivalent amount of dibenzotetrathiafulvalene (IIa).

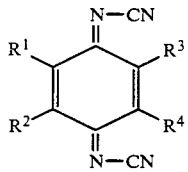

and a compound of the formula

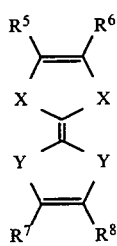
(II)

where $R^1$, $R^2$, $R^3$ and $R^4$ independently of one another are each hydrogen, methyl, ethyl, methoxy, ethoxy, chlorine or bromine, or one of the radicals $R^1$ and $R^2$ or one of the radicals $R^3$ and $R^4$ is phenyl or tert.-butyl, or one of the radicals $R^1$ and $R^2$ and one of the radicals $R^3$ and $R^4$ are each phenyl or tert.-butyl, or $R_1$ and $R_2$ taken together, or $R_3$ and $R_4$ taken together independently form a

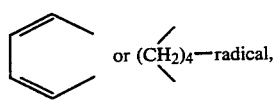

and the fused-on aromatic rings are unsubstituted or monosubstituted or disubstituted by chlorine, bromine or methyl, and $R^5$, $R^6$, $R^7$ and $R^8$ independently of one another are each hydrogen, methyl, ethyl, phenyl, methylphenyl or methoxyphenyl, or $R_5$ and $R_6$ taken together, or $R_7$ and $R_8$ taken together, independently form a

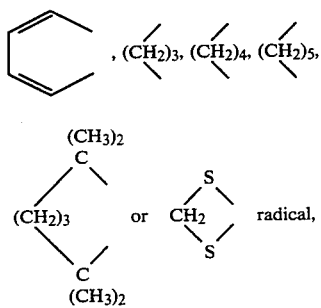

and X and Y independently of one another are each S or Se.

2. A charge transfer complex as claimed in claim 1, wherein the molar ratio of the biscyanodiimine (I) to the tetrathiafulvalene (II) is 1:1 or 1:2.

3. A charge transfer complex as claimed in claim 1, wherein $R^1$ and $R^4$ independently of one another are each chlorine, bromine, methyl, ethyl, tert.-butyl, methoxy or phenyl, $R^2$ and $R^3$ are each hydrogen, methyl or chlorine, $R^5$, $R^6$, $R^7$ and $R^8$ are each hydrogen, or $R^5$ and $R^8$ are each methyl or phenyl and $R^6$ and $R^7$ are each hydrogen, X and Y are each S, and the molar ratio of (I) to (II) is 1:1.

4. A charge transfer complex as claimed in claim 1, wherein $R^1$ and $R^4$ are each hydrogen, chlorine, bromine, methoxy, methyl, tert.-butyl or phenyl, $R^2$ and $R^3$ are each hydrogen, $R_5$ and $R_6$ taken together and $R_7$ and $R_8$ taken together are each

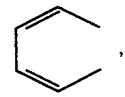

X and Y are each S, and the ratio of (I) to (II) is 1:1 or 1:2.

5. A biscyanimine of the formula

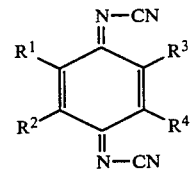

where $R^1$, $R^2$, $R^3$ and $R^4$ independently of one another are each hydrogen, methyl, ethyl, methoxy, ethoxy, chlorine or bromine, or one of the radicals $R^1$ and $R^2$ or one of the radicals $R^3$ and $R^4$ is phenyl or tert.-butyl, or one of the radicals $R^1$ and $R^2$ and one of the radicals $R^3$ and $R^4$ are each phenyl or tert.-butyl, or $R_1$ and $R_2$ taken together, or $R_3$ and $R_4$ taken together, independently form a

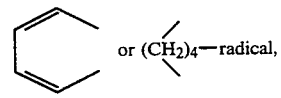

wherein the fused-on aromatic rings are unsubstituted or monosubstituted or disubstituted by chlorine, bromine or methyl.

6. A biscyanimine as claimed in claim 5, wherein $R^1$ and $R^4$ are each hydrogen, methyl, tert.-butyl, phenyl, methoxy, chlorine or bromine and $R^2$ and $R^3$ are each hydrogen, methyl, methoxy or chlorine, or $R^1$ and $R^2$ form

and $R^3$ and $R^4$ are each hydrogen or together form

7. A biscyanimine as claimed in claim 5, wherein $R^1$ and $R^4$ are each hydrogen, methyl, tert.-butyl, phenyl, chlorine or bromine, and $R^2$ and $R^3$ are each hydrogen, or $R^1$ and $R^2$ together form

and $R^3$ and $R^4$ are each hydrogen.

8. A process for the preparation of a biscyanimine of the formula

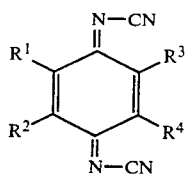

where $R^1$, $R^2$, $R^3$ and $R^4$ independently of one another are each hydrogen, methyl, ethyl, methoxy, ethoxy, chlorine or bromine, or one of the radicals $R^1$ and $R^2$ or one of the radicals $R^3$ and $R^4$ is phenyl or tert.-butyl, or one of the radicals $R^1$ and $R^2$ and one of the radicals $R^3$ and $R^4$ are each phenyl or tert.-butyl, or $R_1$ and $R_2$ taken together, or $R_3$ and $R_4$ taken together, independently form a

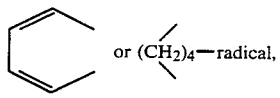

and the fused-on aromatic rings are unsubstituted or monosubstituted or disubstituted by chlorine, bromine or methyl, wherein a quinone of the formula

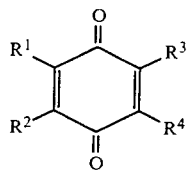

where $R^1$, $R^2$, $R^3$ and $R^4$ have the above meanings, is reacted with bistrimethylsilylcarbodiimide in a molar ratio of 1:2, in the presence of a catalyst and in an inert organic liquid.

9. A process as claimed in claim 8, wherein the catalyst used is cesium fluoride, a crown ether/potassium cyanide or titanium tetrachloride.

10. A process as claimed in claim 9, wherein the catalyst used is titanium tetrachloride.

11. A process as claimed in claim 8, wherein from 2.2 to 3 moles of bistrimethylsilylcarbodiimide are employed per mole of quinone.

12. A process as claimed in claim 9, wherein from 2.2 to 3 moles of bistrimethylsilylcarbodiimide are employed per mole of quinone.

13. A process as claimed in claim 10, wherein from 2.2 to 3 moles of bistrimethylsilylcarbodiimide are employed per mole of quinone.

* * * * *